US00PP32302P3

(12) United States Plant Patent
Romero et al.

(10) Patent No.: US PP32,302 P3
(45) Date of Patent: Oct. 13, 2020

(54) OLIVE TREE NAMED 'I-15'

(50) Latin Name: ***Olea europaea* L.**
Varietal Denomination: I-15

(71) Applicant: Todolivo S.L., Cordova (ES)

(72) Inventors: Luis Rallo Romero, Cordova (ES); Diego Barranco Navero, Cordova (ES); Concepción Muñoz Díez, Cordova (ES); Carlos Trapero Ramírez, Cordova (ES); Pedro Valverde Caballero, Cordova (ES); José Maria Gomez Porras, Cordova (ES)

(73) Assignee: TODOLIVO S.L., Cordova (ES)

( * ) Notice: Subject to any disclaimer, the term of this patent is extended or adjusted under 35 U.S.C. 154(b) by 0 days.

(21) Appl. No.: 16/602,027

(22) Filed: Jul. 24, 2019

(65) Prior Publication Data

US 2020/0037483 P1 Jan. 30, 2020

(30) Foreign Application Priority Data

Jul. 25, 2018 (QZ) ..... PBR 2018/1938

(51) Int. Cl.
*A01H 5/08* (2018.01)
*A01H 6/00* (2018.01)

(52) U.S. Cl.
USPC ..... Plt./158
CPC ..... *A01H 6/00* (2018.05); *A01H 5/08* (2013.01)

(58) Field of Classification Search
USPC ..... Plt./158
CPC ..... A01H 5/08; A01H 5/00; A01H 6/00
See application file for complete search history.

*Primary Examiner* — Keith O. Robinson
(74) *Attorney, Agent, or Firm* — Buchanan Ingersoll & Rooney P.C.

(57) ABSTRACT

A new and distinct variety of olive tree, herein referred to by its cultivar name, 'I-15', is provided which forms an upright to spreading tree growth habit. Fruit with a medium weight is produced. The fruit exhibit black coloration and the fruit nipple is absent or weak. The stone of the fruit of the new variety is of medium weight.

1 Drawing Sheet

Figure 15:
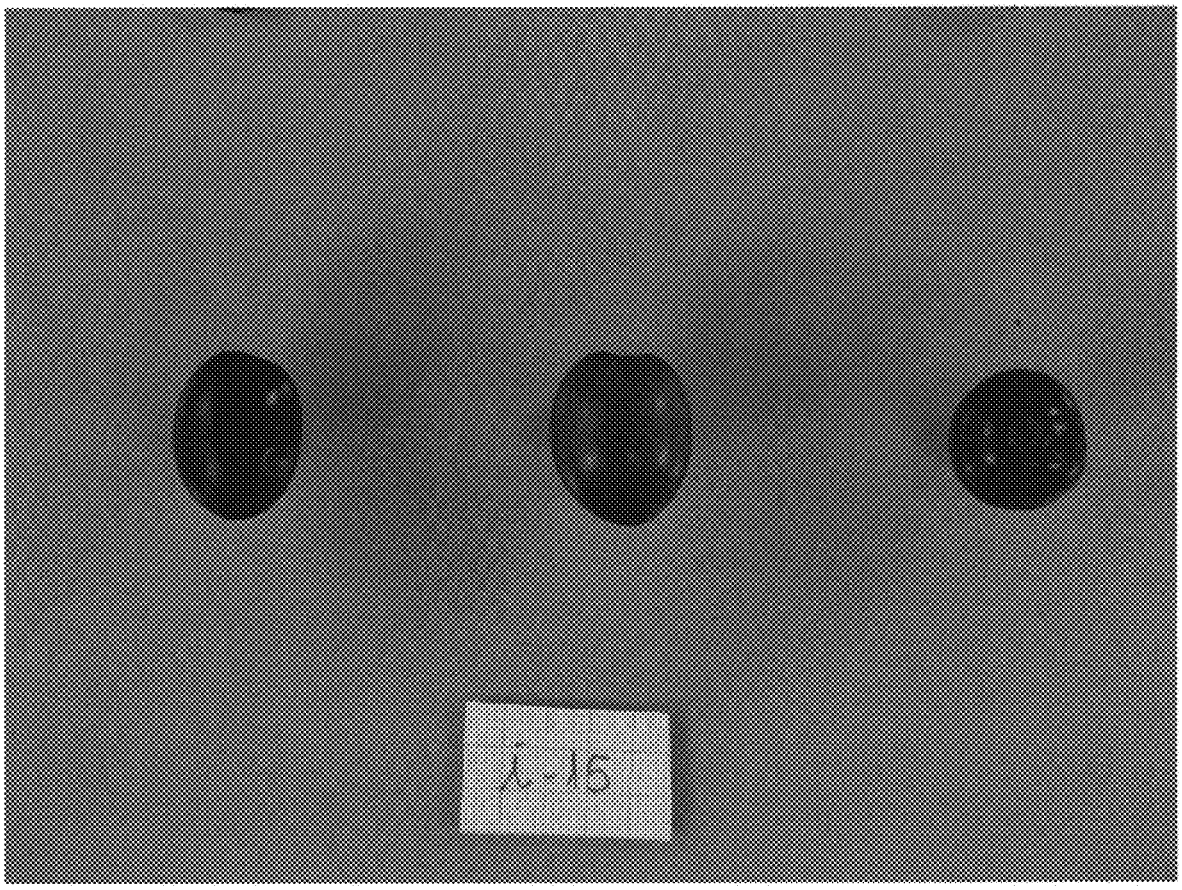

Botanical/commercial classification:
Latin name—*Olea europaea* L.
Common name—Olive tree.
Varietal denomination: 'I-15'.

CROSS-REFERENCE TO RELATED APPLICATIONS

This application claims priority to Plant Breeders' Right Application Number 2018/1938, which was filed at Community Plant Variety Office in the European Union on Jul. 25, 2018, the contents of which are hereby incorporated by reference for all purposes.

SUMMARY OF THE INVENTION

The new variety of olive tree of the present invention was created by a controlled cross in Spain wherein two parents which previously had been studied were crossed in the hope that they would contribute the desired characteristics. The female parent (i.e., seed parent) of the new variety was the 'ARBOSANA' variety (unpatented). The male parent (i.e., pollen parent) was the 'KORONEIKI' variety (unpatented).

The parentage can be summarized as follows:

'ARBOSANA' x 'KORONEIKI'.

The seeds resulting from the above pollination were sown and small plants were obtained which were physically and biologically different from each other. Selective study resulted in the identification of a single plant of the new variety.

The new variety has the same productivity of the 'Arbosana' variety and more than 5 point (%) of oil content. The new variety has a good quality of olive oil that is comparable to the olive oil of the 'Koroneiki' variety. The new variety ripens 1-2 months earlier than the parent varieties 'Arbosana' and 'Koroneiki' with a very good yield efficiency. The new variety's growth habit has a low vigor and compact form, as seen in the 'Arbosana' variety. The non-parental variety that the new variety is most similar to is the 'Arbequina' variety. The new variety's low vigor is less than the 'Arbequina' variety, which is ideal for mechanical harvest. The new variety's ripening is at the same time as the 'Arbequina' variety. The new variety has a more than 5 point (%) of olive oil content and the 'Arbequina' variety has more than 3 point (%) of olive oil content.

It was found that the new variety of the present invention possesses the following combination of characteristics:

(a) forms an upright to spreading growth habit, and
(b) produces fruit with medium weight, which are colored black at full maturity.

The new variety well meets the needs of the horticultural industry.

The new variety can be readily distinguished from related similar varieties.

The new variety has been found to undergo asexual propagation in Spain by vegetative cuttings. Asexual propagation by vegetative cutting in Spain has shown that the characteristics of the new variety are stable and are strictly transmissible by such asexual propagation from one generation to another. Accordingly, the new variety undergoes asexual propagation in a true-to-type manner.

The new variety has been named 'I-15'.

BRIEF DESCRIPTION OF THE PHOTOGRAPH

The accompanying photographs show as nearly true as it is reasonably possible to make the same, in a color illustration of this character, typical specimens of the plant parts of the new variety.

FIG. 1—illustrates specimens of fruit.

DETAILED BOTANICAL DESCRIPTION

The chart used in the identification of the colors is that of The Royal Horticultural Society (R.H.S. Colour Chart, 2007 edition), London, England. The terminology which precedes reference to the chart has been added to indicate the corresponding color in more common terms. The description is based on data collected from a four-year-old specimen during 2019 in Villafranca (Cordoba, Spain).

Plant:
- *Habit*.—Upright to spreading.
- *Vigor*.—Low-medium.
- *Growth habit*.—Spreading.
- *Height*.—Average — 250 cm.
- *Width*.—Average — 160 cm.
- *Branching habit*.—Spreading.

Rooting system:
- *Rooting habit*.—Normal-Dense.
- *Texture*.—Fibrous.
- *Color designation* (*young roots*).—156D.
- *Color designation* (*old roots*).—157A.

Main stems:
- *Quantity*.—Dependent on the management and pruning.
- *Aspect*.—Smooth.
- *Strength*.—Robust.
- *Cross-section*.—Rounded. Small.
- *Circumference* (*average*).—6 cm (diameter) at 50 cm.
- *Surface texture* (*young stems*).—Smooth.
- *Surface texture* (*mature stems*).—Smooth with lenticels.
- *Color designation* (*young stems*).—157A.
- *Color designation* (*mature stems*).—157B.
- *Lenticels*.—Many, 1 mm long, 0.5 mm wide.
- *Internode length* (*average*).—Ranging from 5-12 cm.

Lateral branches:
- *Abundance*.—Abundant.
- *Cross-section*.—Very abundant.
- *Average length*.—80 cm-180 cm.
- *Diameter* (*average*).—1.5 cm.
- *Internode length* (*average*).—2-3 cm.
- *Texture*.—Smooth with raised lenticels.
- *Aspect*.—Outward.
- *Strength*.—Flexible.
- *Color designation* (*young branches*).—196D.
- *Color designation* (*mature branches*).—197D.
- *Pubescence*.—Not pubescence.

Canopy:
- *Density*.—Cup volume is approximately 4.03 $m^3$.

Trunk:
- *Surface texture*.—Smooth.
- *Color designation*.—198D.
- *Circumference* (*average*).—6 cm.

Foliage:
- *Arrangement*.—Opposite.
- *Attachment*.—Petiolate.
- *Division*.—Simple.

Venation:
- *Pattern*.—Pinnate.
- *Color designation* (*adaxial surfaces*).—193D.
- *Color designation* (*abaxial surfaces*).—157A.
- *Average thickness*.—1 mm.

Lamina:
- *Average length*.—Average 52 mm.
- *Average width*.—Average 13 mm.
- *Average thickness*.—1.5-2 mm.
- *Overall shape*.—Slightly elongated.
- *Apex shape*.—Acuminate.
- *Base shape*.—Cuneate.
- *Aspect*.—Straight.
- *Texture* (*adaxial surface*).—Smooth.
- *Texture* (*abaxial surface*).—Slightly pubescent.
- *Color designations*.—Young lamina (adaxial surface) — 141B.
- *Color designations*.—Young lamina (abaxial surface) — 142B.
- *Color designations*.—Mature lamina (adaxial surface) — 143B.
- *Color designations*.—Mature lamina (abaxial surface) — 142B.
- *Twisting*.—No.
- *Margin*.—Entire (smooth).
- *Margin undulation*.—Absent.
- *Serration*.—No.

Petiole:
- *Texture*.—Smooth.
- *Average length*.—2 mm.
- *Average diameter*.—1.20 mm.
- *Color designation*.—142B.
- *Strength*.—Medium.

Inflorescence:
- *Type*.—Panicle.
- *Average length*.—2.5-6.5 cm.
- *Average width*.—1-3 cm.

Peduncle:
- *Average length*.—2.5-6.5 cm.
- *Average diameter*.—1.2 cm.
- *Texture*.—Smooth.
- *Strength*.—Medium.
- *Color designation*.—141D.

Pedicels:
- *Average length*.—2 mm.
- *Average diameter*.—1 mm.
- *Texture*.—Smooth.
- *Strength*.—Medium.
- *Color designation*.—141D.

Flower buds:
- *Shape*.—Globular.
- *Average length*.—2-4 mm.
- *Average diameter*.—2 mm.

Flower:
- *Type*.—Perfect.
- *Number of flowers* (*per inflorescence*).—20-25.
- *Shape*.—Cruciform.
- *Average diameter*.—3-6 mm.
- *Average height*.—2-3 mm.

Calyx:
*Quantity of sepals.*—4.
*Arrangement.*—Rotate.
*Average diameter.*—1 cm.
Sepals:
*Fused or unfused.*—Fused.
*Average length.*—1 mm.
*Average width.*—1 mm.
*Shape.*—Overall — Bell shaped.
*Shape.*—Apex — Obtuse.
*Shape.*—Base — Cuneate.
*Margin.*—Entire.
*Texture.*—Smooth.
*Color designation (upper side).*—18A1.
*Color designation (under side).*—18A1.
Petals:
*Arrangement.*—Rotate.
*Number per flower.*—4.
*Fused or unfused.*—Sympetalous petals fused at the proximal half of the corolla.
*Average width.*—2 mm.
*Shape.*—Overall — Acute.
*Shape.*—Apex — Acute.
*Shape.*—Base — Cuneate.
*Margin.*—Entire.
*Texture.*—Smooth.
*Color when opening (upper surface).*—NN155D.
*Color when opening (under surface).*—NN155D.
*Color when fully opened (upper surface).*—NN155D.
*Color when fully opened (under surface).*—DD155D.
*Color when fading (upper surface).*—Not fading.
*Color when fading (under surface).*—Not fading.
Androecium:
*Stamen (average number).*—2.
*Filament (average length).*—Approximately 0.75 mm.
*Filament (color designation).*—17D1.
*Anther.*—Attachment — Basifixed.
*Anther.*—Shape — Hemispherical.
*Anther (average length).*—1 mm.
*Anther (color designation).*—2A.
*Pollen.*—Amount — abundant.
*Pollen (color designation).*—2A.
Gynoecium:
*Pistil.*—Quantity — 1.
*Stigma.*—Shape — Bifid cone shape.
*Stigma (average length).*—Approximately 0.75 mm.
*Stigma (color designation).*—145D.
*Style (average length).*—Approximately 0.75 mm.
*Style (color designation).*—145D.
*Ovary.*—Position — Superior.
*Ovary.*—Shape — Round.
*Ovary (average diameter).*—Approximately 0.75 mm.
*Ovary (color designation).*—145D.
Fruit:
*Average weight.*—1.69 g (medium).
*Average diameter.*—14.5 mm (medium).
*Average length.*—18 mm (medium).
*Form.*—Ovoidal.
*Suture.*—None.
*Stem cavity size.*—Medium.
*Stem (average length).*—Medium.
*Caliper size.*—Medium.
*Shape.*—Apex Slightly.
*Pistil point.*—Obscure.
*Skin (average thickness).*—Less than 1 mm.
*Skin (surface texture).*—Smooth.
*Skin (tendency to crack).*—None.
*Color designation (ground color).*—62D.
*Color designation (flesh color).*—158C.
*Color designation (surface).*—N77A.
*Color designation (pit).*—144C.
*Juice production description.*—Oil production excellent.
*Flavor description.*—Different/Excellent.
*Ripening.*—Medium.
Stone:
*Quantity.*—1.
*Shape.*—Ovate.
*Type.*—Slightly Asimetric.
*Fibers.*—None.
*Average weight.*—Medium 0.29 g.
*Average length.*—Medium 14 mm.
*Average width.*—Medium 8 mm.
*Average thickness.*—8 mm.
*Shape.*—Apex — Rounded
*Shape.*—Base — Truncate.
*Color designation.*—162B.
*Texture.*—Slightly grooved.
*Mucron.*—Present 2 (1-9 scale).
*Suture.*—Present 2 (1-9 scale).
*Sides.*—Round.
*Ridges.*—Absent.
*Tendency to split.*—None.
*Grooves.*—Approximately 8 fibrovascular grooves with a homogenous distribution.
Development:
*Flowering habit, flowering season.*—1-10 may.
*Harvest season.*—7 months since flowering to harvest.
*Time to produce a fruit bearing tree.*—3 years.
*Chilling requirements; productivity.*—Medium in olive.
*Hardiness.*—The olive oil percentage is between 20-24% in the fruit.
*Plant/fruit disease, pest resistance.*—(Including the Latin name) Resistant to Repilo (*Cycloconium oleaginea*), *Verticillium* (*Verticillium dahlia*) and is tolerant to Tuberculosis (*Pseudomonas savastanoi*).
*Shipping quality, fruit storage life, fruit market use.*—Oil with intense fruitiness and apple-green colour. It has aromas of banana, apple and hints of almond shells. It is sweet and balanced on the palate, slightly bitter and slightly spicier.

The new 'I-15' variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of olive tree characterized by the following combination of characteristics:
(a) forms an upright to spreading growth habit, and
(b) produces fruit with medium weight, which are colored black at full maturity;
substantially as herein shown and described.

* * * * *